United States Patent [19]

Matsumoto et al.

[11] 4,172,051
[45] Oct. 23, 1979

[54] CATALYST FOR PRODUCING METHACRYLIC ACID

[75] Inventors: Mutsumi Matsumoto, Takasaki; Atsushi Sudo, Annaka; Hideki Sugi, Takasaki, all of Japan

[73] Assignee: Nippon Kayaku Kabushiki Kaisha, Tokyo, Japan

[21] Appl. No.: 826,185

[22] Filed: Aug. 19, 1977

[30] Foreign Application Priority Data

Sep. 6, 1976 [JP] Japan .................................. 51-105776

[51] Int. Cl.² .......................... B01J 27/14; C07C 51/24
[52] U.S. Cl. ................................... 252/435; 252/437; 562/534; 562/535
[58] Field of Search ................................ 252/435, 437

[56] References Cited

U.S. PATENT DOCUMENTS

| | | | |
|---|---|---|---|
| 3,156,706 | 11/1964 | Kerr | 252/437 X |
| 3,320,331 | 5/1967 | Gaspar et al. | 252/437 X |
| 3,644,497 | 2/1972 | Mesich | 252/437 X |
| 3,761,516 | 9/1973 | Kloobian | 252/437 X |
| 4,036,780 | 7/1977 | Suzuki et al. | 252/437 |
| 4,049,574 | 9/1977 | Kerr et al. | 252/437 |
| 4,056,487 | 11/1977 | Kerr | 252/435 |
| 4,075,244 | 2/1978 | Akiyama et al. | 252/435 X |

FOREIGN PATENT DOCUMENTS 1468934  3/1969  Fed. Rep. of Germany .
1084143  9/1967  United Kingdom .

Primary Examiner—Delbert E. Gantz
Assistant Examiner—William G. Wright
Attorney, Agent, or Firm—Russell & Nields

[57] ABSTRACT

This invention relates to a process and catalyst for producing methacrylic acid by the oxidation of methacrolein. More specifically, it relates to a process for producing methacrylic acid from methacrolein by oxidizing the same with molecular oxygen or molecular oxygen-containing gas, which is characterized by the use of a composition, as a catalyst, having a heteropolyacid structure and the general formula:

$$Mo_aV_bP_cAl_dY_eO_f$$

wherein Mo, V, P, Al and O represent respectively molybdenum, vanadium, phosphorus, aluminum and oxygen, Y represents one or more elements selected from the groups consisting of copper, tine, cobalt, iron, zirconium, thorium, lead and cerium, and suffixes a, b, c, d, e and f represent the atomic ratio of the elements where, a is 10, b is a number of 3 or less than 3 excluding 0 and, preferably, 0.5 to 2, c is a number of 0.5 to 10 and, preferably, 0.5 to 3, d is a number of 3 or less than 3 excluding 0, preferably, 0.01 to 1.0, e is a number of 0 to 3, preferably, 0.01 to 0.5, and f is usually a number of 35 to 80 being determined depending on the valency and the ratio of number of atoms of other elements.

3 Claims, No Drawings

CATALYST FOR PRODUCING METHACRYLIC ACID

DETAILED DESCRIPTION OF THE INVENTION

This invention relates to a process for producing methacrylic acid by the oxidation of methacrolein. More specifically, it relates to a process for producing methacrylic acid from methacrolein by oxidizing the same with molecular oxygen or molecular oxygen-containing gas, which is characterized by the use of a composition, as a catalyst, having a heteropoly-acid structure and the general formula:

$$Mo_a V_b P_c Al_d Y_e O_f$$

wherein Mo, V, P, Al and O represent respectively molybdenum, vanadium, phosphorus, aluminum and oxygen, Y represents one or more elements selected from the group consisting of copper, tin, cobalt, iron, zirconium, thorium, lead and cerium, and suffixes a, b, c, d, e and f represent the atomic ratio of the elements where, a is 10, b is a number of 3 or less than 3 excluding 0 and, preferably, 0.5 to 2, c is a number of 0.5 to 10 and, preferably, 0.5 to 3, d is a number of 3 or less than 3 excluding 0, preferably, 0.01 to 1.0, e is a number of 0 to 3, preferably, 0.01 to 0.5, and f is usually a number of 35 to 80 being determined depending on the valency and the ratio of number of atoms of other elements. This invention relates as well to the catalyst above described.

Although various catalyst systems have recently been proposed for the catalytic oxidation of methacrolein in gas phase, industrial practice for the oxidation of methacrolein have not yet been attained in contrast to the oxidation of acrolein for the production of acrylic acid. The difficulty arises, it is considered, from the facts that yields of the end products are not so high as those in the production of acrylic acid, the life of the catalyst is too short to maintain a stable catalytic activity for a long time and the like.

Most of the catalysts for the catalytic oxidation of methacrolein in gas phase proposed so far comprise a molybdenum-phosphorus system as a basic component and have a structure of a heteropoly-acid salt composed basically of phosphomolybdate such as of an ammonium salt and an alkali metal salt.

These catalysts have, however, only a low thermal stability as shown by the presence of decomposing peaks at 370°–420° C. in the differential thermal analysis of the heteropoly-acid salt. During continuous reaction for a long time, gradual decomposition of the heteropoly-acid salt structure and crystal growth of molybdenum trioxide are found through X-ray diffraction or the like accompanied by the reduction in the catalytic acitivy. Consequently, none of the catalysts proposed so far has a sufficient catalyst life at all for the industrial use and it enforces to select very mild reaction conditions in order to maintain the catalytic activity for a long time in the catalyst system, being far from satisfying the economical requirements at present.

In view of such low selectivity, low activity and short life of the conventional catalysts for catalytic gas phase oxidation of methacrolein, the inventors of the present application have made an earnest study on eliminating the defects of the catalyst in the industrial use and accomplished this invention on the discovery that a novel catalyst according to this invention can produce methacrylic acid from methacrolein at a high yield and in a stabilized state for a long time.

The catalyst according to this invention is excellent for the industrial use since it has a high activity, selectivity, as well as very long catalyst life.

As foregoings, the catalyst used in this invention contains, various elements and, with all that, has a heteropoly-acid structure as shown by the characteristic peaks at $2\theta = 8.0°$, $8.9°$, $9.3°$ and the like when observed in X-ray diffraction. While the basic component in the structure is a phosphovanadomolybdic acid, other elements incorporated therein are considered to contribute to the improvements in the catalytic acitivity and selectivity, as well as in the stability of the structure by partially replacing the constituent elements in the phosphovanadomolybdic acid and being incorporated into the structure of the heteropoly-acid structure.

The catalyst of this invention is water soluble since it has a heteropoly-acid structure as described above but it may additionally contain water insoluble components such as oxides of the constituent elements and they have no substantial effects on the performance of the catalyst of this invention.

While the catalyst of this invention can be prepared by a general method for preparing usual heteropolyacids, it should particularly be noted to avoid the formation of a heteropoly-acid salt structure such as an ammonium salt of heteropoly-acid in the resulted catalyst.

The catalyst of this invention can be prepared, for example, in the following manner. A heteropoly-acid containing phosphorus element as a central atom can easily be synthesized as conventionally utilized in a quantitative or qualitative analysis for various elements. Accordingly, the catalyst of this invention can also be prepared by reacting the starting materials for the constituent elements in water or in an organic solvent, if necessary, extracting the reaction products, with a suitable organic solvent such as ether, and then evaporating the same to dry. Where salt is produced in the above preparation, it may be converted into relevant acid through conventional ways, for example, by ether extraction from an acidic aqueous solution, ion exchange process and the like.

Particularly preferred preparation methods include those such as dispersing the starting material, for example, oxides or phosphates of the constituent elements into water, reacting the same under heating to dissolve while optionally adding hydrogen peroxide, removing insoluble components, if necessary, and then evaporating the solution to dry, or reacting phosphovanadomolybdic acid with oxides, phosphates, sulfates and the likes of other constituent elements.

Various substances can be used as the starting material for the constituent elements of the catalyst, so long as they are treated in such a process as resulting a catalyst of a heteropoly-acid structure but not of an salt structure.

The starting material usable for the molybdenum component includes, for example, molybdenum trioxide, molybdic acid or its salt, heteromolybdic acid or its salt, molybdenum metal and the like.

The starting material usable for the phosphorus component includes orthophosphoric acid, phosphorous acid, hypophosphorous acid or the salts thereof, phosphorus pentoxide and the like.

The starting material usable for the vanadium component includes vanadium pentoxide, vanadium oxalate, vanadium sulfate, vanadic acid or its salt, vanadium metal and the like.

The starting material for the aluminum component includes relevant oxide, phosphate, nitrate, sulfate and molybdate of aluminum, as well as aluminum metal.

The starting material usable for the component Y includes corresponding oxides, phosphates, nitrates, sulfates, carbonates, molybdates as well as metals of the elements Y.

While the catalyst according to this invention exhibits a high catalytic activity as it is, preferable effects such as improvements in thermal stability and catalyst life and increase in reaction yield can be expected by carrying it on a suitable support. Preferred supports include silicon carbide, α-alumina, aluminum powder, Celite (diatmaceous earth), titania and the like. Those active supports as reacting with heteropoly-acid are not preferable.

The catalyst of this invention is water soluble, which provides advantages in that it can easily be carried on a support and regenerated also with ease by dissolving it again in water after deactivated in a long use for the reaction.

Particularly preferred component Y in the present catalyst includes copper, tin, zirconium, thorium and cerium.

The reactants used for the oxidizing reaction in this invention are methacrolein and molecular oxygen or molecular oxygen-containing gas, wherein the molar ratio of oxygen to methacrolein preferably lies between about 0.5–10 and, most preferably, between about 2–5. It is preferable for smoothly proceeding the reaction to add vaporized water to the starting gas in an amount between about 1–20 and more, preferably, about 5–15 by molar ratio based on methacrolein. The addition of water can promote the desorption of methacrylic acid, the end products, from the surface of the catalyst and control the temperature distribution in the catalyst layer. The starting gas to be supplied may further contain other inert gas, for example, nitrogen, carbon dioxide, saturated hydrocarbon or the like. The gaseous reaction products containing methacrolein obtained by catalytic oxidation of isobutylene or tertiary butanol can be used as they are as the starting material.

The reaction temperature for practicing the process of this invention is preferably between about 200°–380° C. and, more preferably, about 250°–350° C. The amount of the starting gas to be supplied is preferably between about 100–5000 $Hr^{-1}$ and, more preferably, about 500–3000 $Hr^{-1}$ in the space velocity (SV) based on the NTP standard. Since the increase in the space velocity (SV) has no substantial effects on the results of the reaction where the catalyst of this invention is employed, the reaction can be conducted at a high space velocity. While the reaction of this invention can be effected at a pressure either above or below the atmospheric pressure, it is suitably effected generally at a pressure near the atmospheric pressure. Preferred pressure for the reaction in this invention lies between about 1–5 atm.

The reaction of this invention can be effected in any desired types of reactor such as of a fixed bed, a fluidized bed or a moving bed type.

This invention is to be described specifically hereinafter referring to the examples thereof but it should be understood that the invention is no way restricted to such examples.

In the examples, no particular references are made for the details of oxygen in the catalyst composition since they are determined in accordance with the atomic ratio and valency of other elements.

The conversion of methacrolein, the yield of methacrylic acid and the selectivity to methacrylic acid are defined as follows:

Conversion of methacrolein (%) = $\frac{\text{methacrolein reacted (mol)}}{\text{methacrolein supplied (mol)}} \times 100$ Yield of methacrylic acid (%) = $\frac{\text{methacrylic acid resulted (mol)}}{\text{methacrolein supplied (mol)}} \times 100$ Selectivity to methacrylic acid (%) = $\frac{\text{yield of methacrylic acid}}{\text{conversion of methacrolein}} \times 100$

EXAMPLE 1

100 g of molybdenum trioxide, 6.3 g of vanadium pentoxide, 0.36 g of alumina, and 8.0 g of orthophosphoric acid were dispersed or dissolved into 1000 ml of deionized water and kept at about 50° C. over 24 hours while occasionally adding an aqueous solution of hydroperoxide to produce a clear orange red solution. After removing a slight amount of insoluble contents, it was evaporated to dry on a hot bath. The dried products thus obtained (catalyst) had a composition: $Mo_{10}V_1Al_{0.1}P_1$ and were confirmed to be a heteropoly-acid by the observation of diffraction peaks at $2\theta = 8.0°$, $8.9°$, $9.3°$ and the like through X-ray diffraction. It was grounded into 6–9 mesh and then charged into a tubular reactor made of pyrex glass of 18 mm in inside diameter and immersed in a fluidized bath. Starting gas of a composition wherein methacrolein:oxygen:nitrogen:water vapor=1:2:18:7 (in molar ratio) was caused to pass through the tubular reactor at SV=1200 $Hr^{-1}$ (NTP standard) and subjected to oxidation reaction at a reaction temperature of 320° C. for 30 days. The results are shown in Table 1.

EXAMPLE 2

100 g of molybdenum trioxide, 6.3 g of vanadium pentoxide, 0.36 g of alumina, 2.0 g of copper phosphate and 7.0 g of orthophosphoric acid were used as the starting material to prepare dried products: $Mo_{10}V_1Al_{0.1}Cu_{0.2}P_1$ in the same procedure as in Example 1 and a continuous reaction was conducted using the above catalyst under the same conditions as in Example 1. The results are as shown in Table 1.

EXAMPLES 3–9

2.0 g of copper phosphate in Example 2 was replaced in each of the examples with 1.5 g of tin phosphate, 1.2 g of cobalt phosphate, 1.4 g of ferric phosphate, 0.86 g of zirconium oxide, 1.8 g of thorium oxide, 1.6 g of trilead tetroxide and 1.2 g of cerium oxide respectively and dried products having compositions as shown in Table 1 were obtained. A series of continuous reactions were conducted using the above catalysts under the same reaction conditions as in Example 1. The results are as shown in Table 1.

Table 1

| Example | Catalyst Composition | Reaction time (days) | Conversion of methacrolein (%) | Yield of methacrylic acid (%) | Selectivity to methacrylic acid (%) |
|---|---|---|---|---|---|
| 1 | $Mo_{10}V_1Al_{0.1}P_1$ | 1 | 74.5 | 57.0 | 76.5 |
|  |  | 30 | 74.1 | 56.5 | 76.2 |
| 2 | $Mo_{10}V_1Al_{0.1}Cu_{0.2}P_1$ | 1 | 85.0 | 67.6 | 79.5 |
|  |  | 30 | 85.5 | 67.5 | 79.0 |
| 3 | $Mo_{10}V_1Al_{0.1}Sn_{0.1}P_1$ | 1 | 76.5 | 59.0 | 77.1 |
|  |  | 30 | 76.1 | 58.5 | 76.9 |
| 4 | $Mo_{10}V_1Al_{0.1}Co_{0.1}P_1$ | 1 | 77.5 | 58.1 | 75.0 |
|  |  | 20 | 77.5 | 57.7 | 74.5 |
| 5 | $Mo_{10}V_1Al_{0.1}Fe_{0.1}P_1$ | 1 | 78.5 | 60.1 | 76.5 |
|  |  | 18 | 78.8 | 60.3 | 76.5 |
| 6 | $Mo_{10}V_1Al_{0.1}Zr_{0.1}P_1$ | 1 | 77.0 | 60.1 | 78.0 |
|  |  | 30 | 76.8 | 59.5 | 77.5 |
| 7 | $Mo_{10}V_1Al_{0.1}Th_{0.1}P_1$ | 1 | 79.7 | 62.6 | 78.5 |
|  |  | 30 | 79.5 | 62.4 | 78.5 |
| 8 | $Mo_{10}V_1Al_{0.1}Pb_{0.1}P_1$ | 1 | 75.5 | 58.1 | 77.0 |
|  |  | 30 | 75.5 | 57.8 | 76.5 |
| 9 | $Mo_{10}V_1Al_{0.1}Ce_{0.1}P_1$ | 1 | 78.8 | 61.1 | 77.5 |
|  |  | 30 | 78.5 | 60.4 | 77.0 |

EXAMPLES 10–13

1.5 g of tin phosphate, 1.2 g of cerium oxide, 1.8 g of thorium oxide and 0.86 g of zirconium oxide were further added respectively to the preparation material in Example 2 and the dried products as shown in Table 2 were prepared in the same way as in Example 2. Continuous reactions were conducted using the above catalysts under the same reaction conditions as in Example 1. The results are as shown in Table 2.

Table 2

| Example | Catalyst composition | Reaction time (days) | Conversion of methacrolein (%) | Yield of methacrylic acid (%) | Selectivity to methacrylic acid (%) |
|---|---|---|---|---|---|
| 10 | $Mo_{10}V_1Al_{0.1}Cu_{0.2}Sn_{0.1}P_1$ | 1 | 85.5 | 67.3 | 78.7 |
|  |  | 30 | 84.0 | 65.3 | 77.7 |
| 11 | $Mo_{10}V_1Al_{0.1}Cu_{0.2}Ce_{0.1}P_1$ | 1 | 82.0 | 66.0 | 80.5 |
|  |  | 30 | 81.5 | 65.2 | 80.0 |
| 12 | $Mo_{10}V_1Al_{0.1}Cu_{0.2}Th_{0.1}P_1$ | 1 | 83.5 | 68.5 | 82.0 |
|  |  | 30 | 82.0 | 66.8 | 81.5 |
| 13 | $Mo_{10}V_1Al_{0.1}Cu_{0.2}Zr_{0.1}P_1$ | 1 | 77.5 | 64.3 | 83.0 |
|  |  | 30 | 77.0 | 63.8 | 82.9 |

EXAMPLES 14–15

The dried products as shown in Table 3 were prepared as in Example 1 and continuous reactions were conducted using the above catalysts in the same reaction conditions as in Example 1. The results are shown in Table 3.

Table 3

| Example | Catalyst composition | Reaction time (days) | Conversion of methacrolein (%) | Yield of methacrylic acid (%) | Selectivity to methacrylic acid (%) |
|---|---|---|---|---|---|
| 14 | $Mo_{10}V_2Al_{0.1}P_1$ | 1 | 68.5 | 51.4 | 75.0 |
|  |  | 50 | 69.5 | 52.2 | 75.1 |
| 15 | $Mo_{10}V_1Al_{0.1}P_3$ | 1 | 73.0 | 54.8 | 75.0 |
|  |  | 30 | 72.8 | 54.8 | 75.3 |

EXAMPLE 16

100 g of phosphovanadomolybdic acid ($H_4Mo_{11}V_1PO_{40}.11H_2O$) was dissolved into 500 ml of deionized water, to which 0.62 g of aluminum phosphate ($AlPO_4$) was added and they were reacted to dissolve under heating at about 50° C. while stirring. A clear orange red solution obtained was evaporated to dry to obtain dried products having a composition: $Mo_{10}V_{0.9}Al_{0.09}P_1$. Reaction was conducted using the above catalyst at a bath temperature of 320° C. as in Example 1 to obtain the following results.

Conversion of methacrolein: 75.5%
Yield of methacrylic acid: 55.4%
Selectivity to methacrylic acid: 73.4%

EXAMPLES 17–22

Dried products having compositions as shown in Table 4 were obtained as in Examples 1–9 and continuous reactions were conducted using the above catalysts and under the same reaction conditions as in Example 1. The results are shown in Table 4.

Table 4

| Example | Catalyst composition | Reaction time (days) | Conversion of methacrolein (%) | Yield of methacrylic acid (%) | Selectivity to methacrylic acid (%) |
|---|---|---|---|---|---|
| 17 | $Mo_{10}V_1Al_1P_1$ | 1 | 78.2 | 56.4 | 72.1 |
|  |  | 30 | 78.0 | 56.6 | 72.5 |
| 18 | $Mo_{10}V_2Al_{0.1}Sn_{0.2}P_1$ | 1 | 70.3 | 53.6 | 76.2 |
|  |  | 30 | 71.0 | 54.0 | 76.0 |
| 19 | $Mo_{10}V_1Al_{0.05}Ce_{0.1}P_1$ | 1 | 76.5 | 59.3 | 77.5 |
|  |  | 30 | 77.0 | 59.3 | 77.0 |
| 20 | $Mo_{10}V_1Al_1Cu_{0.2}P_1$ | 1 | 80.3 | 59.0 | 73.5 |
|  |  | 30 | 80.5 | 59.0 | 73.6 |
| 21 | $Mo_{10}V_1Al_{0.1}Cu_2P_1$ | 1 | 87.3 | 62.0 | 71.0 |
|  |  | 30 | 86.5 | 61.8 | 71.5 |
| 22 | $Mo_{10}V_1Al_{0.05}Cu_{0.05}P_1$ | 1 | 81.2 | 64.0 | 78.8 |
|  |  | 30 | 82.5 | 65.2 | 79.0 |

Comparison Example 1

Dired products having a composition, $Mo_{10}V_1P_1$ were obtained in the same procedures as in Example 1 but with no addition of the 0.36 g of alumina and a similar continuous reaction was conducted using the above catalyst. The results are as shown in Table 5.

Comparison Example 2

A 28% aqueous ammonia solution was added to the clear orange red solution obtained in Example 1 (pH=1.0) to adjust the pH value to 5.3. After evaporating the solution to dry, the dried products were ground into 6-9 mesh and calcined in air at 380° C. for 8 hours. The catalyst prepared had a composition: $(NH_4)_{1.5}Mo_{10}V_1Al_{0.1}P_1$ and the formation of an ammonium salt of heteropoly-acid was confirmed from X-ray diffraction and IR absorption spectrum. A similar continuous reaction was conducted using the above catalyst. The results are shown in Table 5.

Table 5

| Comparision example | Catalyst composition | Reaction time (days) | Conversion of methacrolein (%) | Yield of methacrylic acid (%) | Selectivity to methacrylic acid (%) |
| --- | --- | --- | --- | --- | --- |
| 1 | $Mo_{10}V_1P_1$ | 1 | 65.0 | 49.1 | 75.5 |
|   |   | 15 | 54.5 | 39.3 | 72.1 |
| 2 | $(NH_4)_{1.5}Mo_{10}V_1Al_{0.1}P_1$ | 1 | 83.0 | 62.3 | 75.0 |
|   |   | 15 | 63.0 | 45.5 | 72.3 |

What is claimed is:

1. A catalyst having a heteropoly-acid structure and the general formula:

$$Mo_aV_bP_cAl_dY_eO_f$$

wherein Mo, V, P, Al and O represent respectively molybdenum, vanadium, phosphorus, aluminum and oxygen, Y represents one or more elements selected from the group consisting of copper, tin, cobalt, iron, zirconium, thorium, lead and cerium and a, b, c, d, e and f represent the atomic ratio of the elements where, a is 10 b is a number of 3 or less than 3 excluding 0, c is a number of 0.5 to 10, d is a number of 3 or less than 3 excluding 0, e is a number of 0 to 3 and f is a number determined depending on the valency and atomic ratio of other elements.

2. The catalyst according to claim 1, where a is 10, b is a number of 0.5 to 2, c is a number of 0.5 to 3, d is a number of 0.01 to 1.0 and e is a number of 0.01 to 0.5.

3. The catalyst according to claim 1, wherein Y represents one or more elements selected from the group consisting of copper, tin, zirconium, thorium and cerium.

* * * * *